(12) United States Patent
Wu et al.

(10) Patent No.: US 9,011,770 B2
(45) Date of Patent: *Apr. 21, 2015

(54) DEVICE FOR DETECTING ANALYTES IN FLUID SAMPLES

(75) Inventors: Yuzhang Wu, Hangzhou (CN); Haipeng Hu, Hangzhou (CN); Jielin Dai, Hangzhou (CN); Lijian Gou, HangZhou (CN)

(73) Assignee: Alere Switzerland GmbH, Zug (CH)

( * ) Notice: Subject to any disclaimer, the term of this patent is extended or adjusted under 35 U.S.C. 154(b) by 1763 days.

This patent is subject to a terminal disclaimer.

(21) Appl. No.: 11/260,496

(22) Filed: Oct. 26, 2005

(65) Prior Publication Data

US 2007/0092402 A1     Apr. 26, 2007

(51) Int. Cl.
| G01N 21/00 | (2006.01) |
| G01N 33/543 | (2006.01) |
| B01L 3/00 | (2006.01) |
| A61B 10/00 | (2006.01) |

(52) U.S. Cl.
CPC ......... *G01N 33/54366* (2013.01); *A61B 10/007* (2013.01); *B01L 3/502* (2013.01); *B01L 2300/0663* (2013.01); *B01L 2300/087* (2013.01); *B01L 2400/0478* (2013.01)

(58) Field of Classification Search
CPC .......................... G01N 21/00; B01L 2300/087
See application file for complete search history.

(56) References Cited

U.S. PATENT DOCUMENTS

| 4,409,989 | A | 10/1983 | Larribas |
| 5,238,652 | A | 8/1993 | Sun |
| 5,464,775 | A | 11/1995 | Smith |
| 5,606,116 | A | 2/1997 | Yoneda |
| 5,874,216 | A | 2/1999 | Mapes |
| 5,942,442 | A | 8/1999 | Di Cesare |
| D423,110 | S | 4/2000 | Cipkowski |
| D430,303 | S | 8/2000 | Cipkowski |
| 6,150,178 | A * | 11/2000 | Cesarczyk et al. ............ 436/165 |
| 6,291,178 | B1 | 9/2001 | Schnider |
| 6,372,515 | B1 | 4/2002 | Casterlin |
| 6,376,195 | B1 | 4/2002 | Mapes |
| 6,383,736 | B1 | 5/2002 | Titmas |
| 6,406,922 | B2 | 6/2002 | Casterlin |
| 6,464,939 | B1 * | 10/2002 | Bachand et al. ................ 422/58 |
| 6,514,461 | B1 * | 2/2003 | Lappe et al. ................. 422/68.1 |
| 6,514,769 | B2 | 2/2003 | Lee |
| 6,528,323 | B1 | 3/2003 | Thayer |

(Continued)

FOREIGN PATENT DOCUMENTS

| EP | 0709675 | 3/2002 |
| EP | 1028806 | 7/2003 |

(Continued)

*Primary Examiner* — Jyoti Nagpaul
(74) *Attorney, Agent, or Firm* — DLA Piper LLP (US)

(57) ABSTRACT

The present invention provides a device for detecting the presence of an analyte in a liquid sample. The device has an opening for introducing the liquid sample into a first chamber for collecting the liquid sample, and a second chamber connected to the first chamber by a passageway and containing a test element. The device also has a third chamber connected to the second chamber by a channel and containing a movable member having first and second positions. The third chamber is divided by the movable member into first and second zones, and the first zone has a vent hole. The movable member is in contact with at least one wall of the third chamber to prevent gas communication between the first and second zones.

13 Claims, 5 Drawing Sheets

(56) References Cited

U.S. PATENT DOCUMENTS

| | | |
|---|---|---|
| 6,548,019 B1 | 4/2003 | Lee |
| 6,616,893 B1 | 9/2003 | Pham |
| 6,663,831 B2 | 12/2003 | Konecke |
| 6,730,268 B2 | 5/2004 | Lee |
| 7,114,403 B2 * | 10/2006 | Wu et al. .................. 73/864.72 |
| 8,511,149 B2 * | 8/2013 | Lv ................................ 73/64.56 |
| 2002/0001854 A1 | 1/2002 | Lee |
| 2002/0081233 A1 * | 6/2002 | Lappe et al. ............... 422/82.05 |
| 2002/0146346 A1 | 10/2002 | Konecke |
| 2003/0007892 A1 | 1/2003 | Smith |
| 2003/0027359 A1 * | 2/2003 | Hudak et al. ................. 436/518 |
| 2003/0064526 A1 * | 4/2003 | Niedbala et al. ............. 436/165 |
| 2003/0118479 A1 * | 6/2003 | Quirk et al. ..................... 422/58 |
| 2003/0129088 A1 | 7/2003 | Lee |
| 2004/0132091 A1 | 7/2004 | Ramsey |
| 2004/0133128 A1 | 7/2004 | Guan |
| 2004/0184965 A1 | 9/2004 | Smith |
| 2005/0008538 A1 | 1/2005 | Anderson |
| 2005/0009203 A1 | 1/2005 | Wong |
| 2005/0053519 A1 | 3/2005 | Smith |
| 2005/0106750 A1 | 5/2005 | Tung |
| 2005/0112024 A1 | 5/2005 | Guo |
| 2005/0119589 A1 * | 6/2005 | Tung et al. ..................... 600/584 |
| 2005/0202568 A1 * | 9/2005 | Tung et al. ..................... 436/169 |
| 2006/0029517 A1 * | 2/2006 | Hartselle ......................... 422/61 |
| 2009/0117665 A1 * | 5/2009 | Tung et al. ..................... 436/501 |

FOREIGN PATENT DOCUMENTS

| | | |
|---|---|---|
| WO | WO0029111 | 5/2000 |
| WO | WO0062060 | 10/2000 |
| WO | WO0063697 | 10/2000 |
| WO | WO0165230 | 9/2001 |
| WO | WO0189697 | 11/2001 |
| WO | WO0224337 | 3/2002 |
| WO | WO02082040 | 10/2002 |
| WO | WO2005006959 | 1/2005 |
| WO | WO2005050168 | 6/2005 |
| WO | WO2005050169 | 6/2005 |

* cited by examiner

DEVICE FOR DETECTING ANALYTES IN FLUID SAMPLES

FIELD OF THE INVENTION

The present invention relates to devices for the detection of analytes in fluid samples.

BACKGROUND OF THE INVENTION

The following Background of the Invention is intended to aid the reader in understanding the invention and is not admitted to be prior art.

In the health-care industry, diagnostic testing of body fluids is a common place activity. Employers, government agencies, sports teams and other organizations have also become increasingly involved in diagnostic testing to maintain safety in the workplace and to ensure compliance with laws, rules and regulations.

It is generally necessary to utilize devices for collecting body fluids, such as urine, and to detect the presence of a predetermined analyte (e.g. a drug and/or metabolite thereof, or an indicator of disease). Such testing devices generally require that a sample be placed in a sample container and that a technician manually insert and submerge a portion of a testing strip into the sample, and then withdraw it to read the result. With the potential for contact with the sample by the technician and its associated health and contamination risks, a sealed receptacle for preventing contact is desirable. Various means have been proposed for reducing the risk of contact as shown in U.S. Pat. No. 4,976,923, U.S. Pat. No. 5,429,804, and U.S. Pat. No. 6,726,879, which utilize testing devices having test strips mounted in their lids. In use, the container is inverted or tilted so that the sample can wet the strips to perform the test.

Recently, the use of testing devices by other than health care professionals has increased. Due to the fact that these tests are increasingly performed and evaluated by relatively unskilled technicians, the device should be simple to operate to ensure adequate submersion of the test strip and provide accurate results.

Therefore, a continuing need exists for testing devices that require minimum manual operation while ensuring accurate and reliable test results.

SUMMARY OF THE INVENTION

The present invention provides a device for detecting the presence of an analyte in a liquid sample. The device has an opening for introducing the liquid sample into a first chamber for collecting the liquid sample, and a second chamber connected to the first chamber by a passageway and containing a test element. The device also has a third chamber connected to the second chamber by a channel and containing a movable member having first and second positions. The third chamber is divided by the movable member into first and second zones, and the first zone has a vent hole. The movable member is in contact with at least one wall of the third chamber to prevent gas communication between the first and second zones.

In one embodiment the device can also have a lid for closing the opening. The test element can be an assay card containing one or more assay test strips.

In one embodiment of the device the movable member is a plunger. The plunger can contain a seal in contact with at least one wall of the third chamber to prevent gas communication between the first and second zones of the third chamber. The third chamber can also have a bottom, and in one embodiment the vent hole is situated on the bottom of the third chamber. In one embodiment the plunger has a push bar extending towards the opening of the container. The lid can have a surface that contacts and depresses the push bar when the lid is applied to the opening.

In various embodiments of the device the passageway has a diameter of less than 10 mm, or less than 9 mm, or less than 8 mm, or less than 7 mm, or less than 6 mm, or less than 5 mm, or less than 4 mm, or less than 3 mm.

In another aspect the present invention provides methods for detecting the presence of an analyte in a liquid sample. The methods involve introducing a liquid sample into a test device as described herein, causing the movable member to move from the first position to the second position and thereby causing a volume of air to be drawn from the second chamber into the third chamber, and thereby causing a volume of liquid to be drawn from the first chamber through the passageway and into the second chamber to contact the test element, and detecting the presence of the analyte in the sample.

In one embodiment the methods involve contacting the lid with the push bar and depressing the push bar as the lid is applied to the device, and thereby causing the movable member to move from the first position to the second position. In one embodiment depressing the push bar and moving the movable member from the first position to the second position causes a negative air pressure gradient to form in the third chamber and the volume of air to be drawn from the second chamber into the third chamber. The movement of the volume of air from the second chamber to the third chamber can be the cause of a negative air pressure gradient forming in the second chamber. By formation of a negative air pressure gradient is meant that a vacuum forms in one chamber, causing air to be "pulled" into the chamber from another chamber in order to fill the vacuum created. The air pressure gradient refers to a difference in internal air pressures between two chambers.

In one embodiment the negative air pressure gradient in the second chamber causes the fluid sample to flow from the first chamber through the passageway to the second chamber, and thereby to contact the test element. Depressing the push bar and moving the movable member from the first position to the second position can cause a volume of air to escape from the first zone through the vent hole.

The summary of the invention described above is not limiting and other features and advantages of the invention will be apparent from the following detailed description, as well as from the claims.

DETAILED DESCRIPTION

Figure 1:
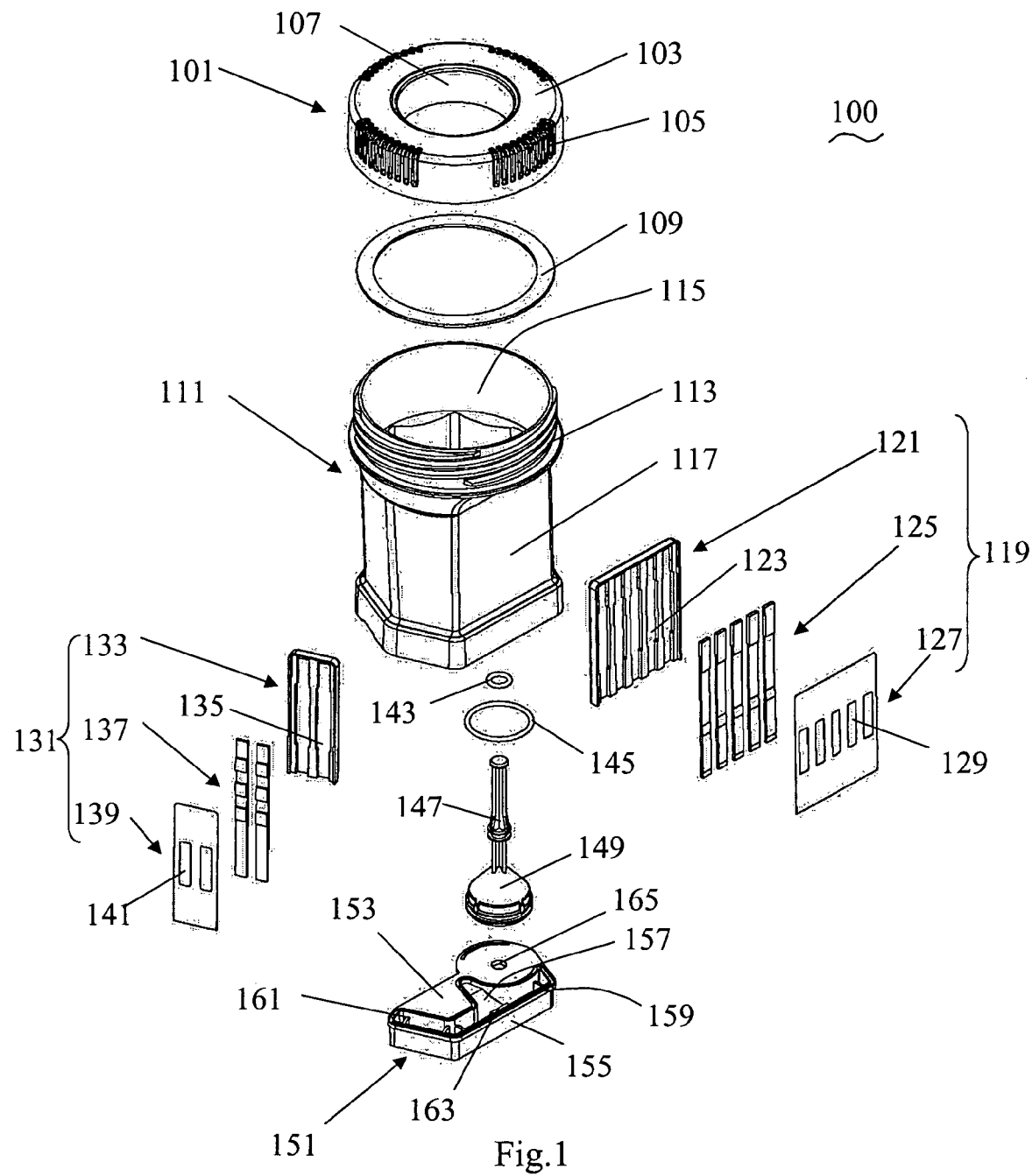
FIG. 1 is an exploded perspective view of the device in accordance with the present invention.

The present invention provides devices and methods for determining the presence or amount of an analyte in a liquid sample. In one embodiment the device takes the form of a cup, which receives a liquid sample for analysis. In one embodiment the liquid sample is urine. The analyte can be any analyte, for example, glucose, a drug of abuse or a metabolite thereof.

The device utilizes a system of chambers to move liquid sample through the device and detect the presence or amount of an analyte in the samples. In one embodiment the device has three chambers, and liquid sample can be moved from one chamber to another by force of air pressure. The surface tension of the liquid sample can be used to hold the liquid in one chamber until the user is prepared to move the sample to an adjacent chamber by application of air pressure to the chambers. In various embodiments the air pressure can take the form of an increase or a decrease (e.g., formation of a vacuum) in internal air pressure. The different chambers of the device are connected by passageways, channels, and vent holes, which allow for the transfer of air pressure and liquid between the chambers. The device also has a movable member situated in one of the chambers. In one embodiment the movable member is a plunger, and the chamber is a cylinder that houses the plunger. When the plunger is moved from a first position to a second position, air is forced out of the third chamber and creates a vacuum that is transferred to the second chamber, which causes a break in surface tension of liquid situated in the first chamber, and thereby causes liquid to flow from the first to the second chamber. By cylinder is meant a structure containing the movable member and within which the movable member is moved from a first position to a second position. When the chamber is a cylinder, it need not have a perfectly cylindrical shape in all embodiments, but can vary in shape and size, or take one shape at one portion and another shape at another portion, as long as it still performs the functions required by the assay.

In one embodiment the test element of the device is situated in the second chamber and analysis of the liquid sample therefore begins. In the embodiment depicted in the Figures, the movable member has the form of a plunger-type structure having a generally cylindrical shape. But in other embodiments the movable member can take any suitable shape.

Analytes

A variety of analytes can be detected or quantified by the test elements in the present invention. The analyte may be an infectious agent or indicative of an infected state. The analyte may be a drug (for example a drug of abuse), a hormone, a protein, a nucleic acid molecule, an etiological agent, or a specific binding pair member. The term "drug of abuse" (DOA) refers to a drug that is taken for non-medicinal reasons (usually for mind-altering effects). The abuse of such drugs can lead to physical and mental damage and (with some substances) dependence, addiction and/or death. Examples of DOAs include cocaine; amphetamines (e.g., black beauties, white bennies, dextroamphetamines, dexies, beans); methamphetamines (crank, meth, crystal, speed); barbiturates (Valium®, Roche Pharmaceuticals, Nutley, N.J.); sedatives (i.e. sleep-aids); lysergic acid diethylamide (LSD); depressants (downers, goofballs, barbs, blue devils, yellow jackets, ludes); tricyclic antidepressants (TCA, e.g., imipramine, amitriptyline and doxepin); phencyclidine (PCP); tetrahydrocannabinol (THC, pot, dope, hash, weed, etc.); and opiates (e.g., morphine, opium, codeine, heroin, oxycodone). Legal drugs that are taken for medical reasons, but on which overdose can easily occur may also be tested for using these test strips, for example, tricyclic antidepressants (imipramine and the like) and over the counter products containing acetaminophen.

Test Elements

The test element can conveniently be selected as lateral flow test strips, which are widely available for testing a broad range of analytes. However, any suitable test element can be used in the present invention.

A variety of test elements can be incorporated into the present invention. One type of test element is a test strip. Test strips are available in a variety of formats, such as immunoassay or chemical test format, for detecting analytes of interest in a sample, such as a drug of abuse or a metabolite suggestive of health status. Test strips can also be configured for either noncompetitive or competitive assay formats. In some formats, the test strips have a bibulous material having a sample application zone, a reagent zone, and a test result zone. The sample is applied to the sample application zone and flows into the reagent zone by capillary action. In the reagent zone, the sample dissolves and mixes with reagents necessary for detection of the analyte (if present). The sample, now carrying the reagents, continues to flow to the test results zone. Additional reagents are immobilized in the test results zone, such as a specific binding molecule for the analyte. These reagents react with and bind the analyte (if present) or one of the first reagents from the reagent zone. Labels for providing the detectable signal can be present in the reagent zone, or in a separate label zone.

Typically, in noncompetitive formats, a signal is produced if the sample contains the analyte, and no signal is produced if the analyte is not present. In competitive formats, a signal can be produced if no analyte is present, and no signal if analyte is present.

When the test element is a test strip, it may be made of bibulous or non-bibulous material. A test strip can include more than one material, which are then in fluid communication. One material of a test strip may be overlaid on another material of the test strip, such as for example, filter paper overlaid on nitrocellulose. Alternatively or in addition, a test strip may include a region comprising one or more materials followed by a region comprising one or more different materials. In this case, the regions are in fluid communication and may or may not partially overlap one another. The material or materials of the test strip can be bound to a support or solid surface such as a supporting sheet of plastic, to increase its handling strength.

In embodiments where the analyte is detected by a signal producing system, such as by one or more enzymes that specifically react with the analyte, one or more components of the signal producing system can be bound to the analyte detection zone of the test strip material in the same manner as specific binding members are bound to the test strip material, as described above. Alternatively or in addition, components of the signal producing system that are included in the sample application zone, the reagent zone, or the analyte detection zone of the test strip, or that are included throughout the test strip, may be impregnated into one or more materials of the test strip. This can be achieved either by surface application of solutions of such components or by immersion of the one or more test strip materials into solutions of such components. Following one or more applications or one or more immersions, the test strip material is dried. Alternatively or in addition, components of the signal producing system that are included in the sample application zone, the reagent zone, or the analyte detection zone of the test strip, or that are included throughout the test strip, may be applied to the surface of one or more test strip materials of the test strip as was described for labeled reagents.

The zones can be arranged as follows: sample application zone, one or more reagent zones, one or more test results determination zones, one or more control zones, one or more adulteration zones, and fluid absorbing zone. If the test results determination zone includes a control zone, preferably it follows the analyte detection zone of the test result determination zone. All of these zones, or combinations thereof, can be provided in a single strip of a single material. Alternatively, the zones are made of different materials and are linked together in fluid communication. For example, the different zones can be in direct or indirect fluid communication. In this instance, the different zones can be jointed end-to-end to be in fluid communication, overlapped to be in fluid communication, or be communicated by another member, such a joining material, which is preferably bibulous such as filter paper, fiberglass or nitrocellulose. In using a joining material, a joining material may communicate fluid from end-to-end joined zones or materials including such zones, end-to-end joined zones or materials including such zones that are not in fluid communication, or join zones or materials that include such zones that are overlapped (such as but not limited to from top to bottom) but not in fluid communication.

Devices

Figure 2:
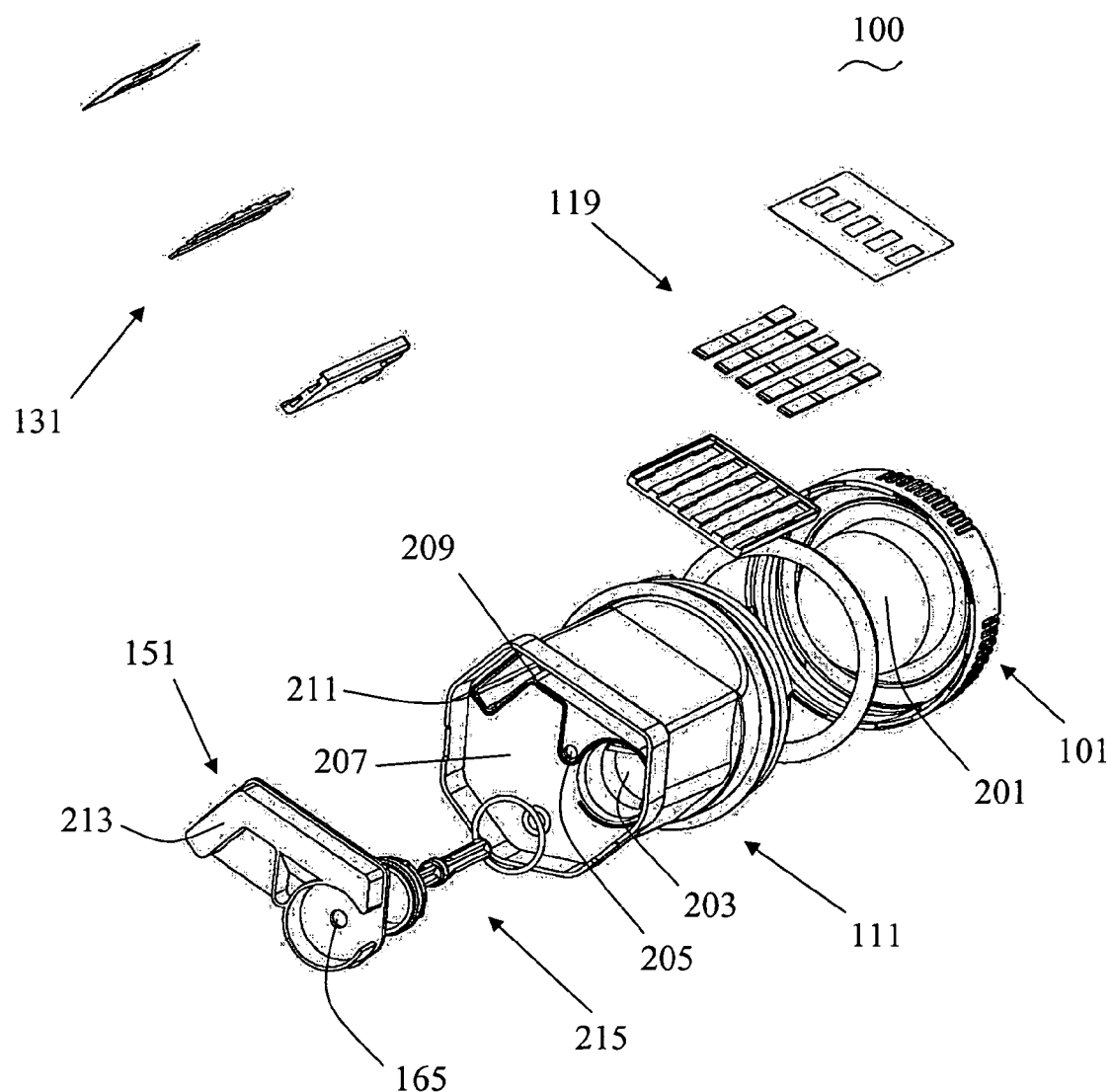
FIG. 2 is another exploded perspective view of the device in accordance with the present invention from a different aspect.
Figures 3, 4:
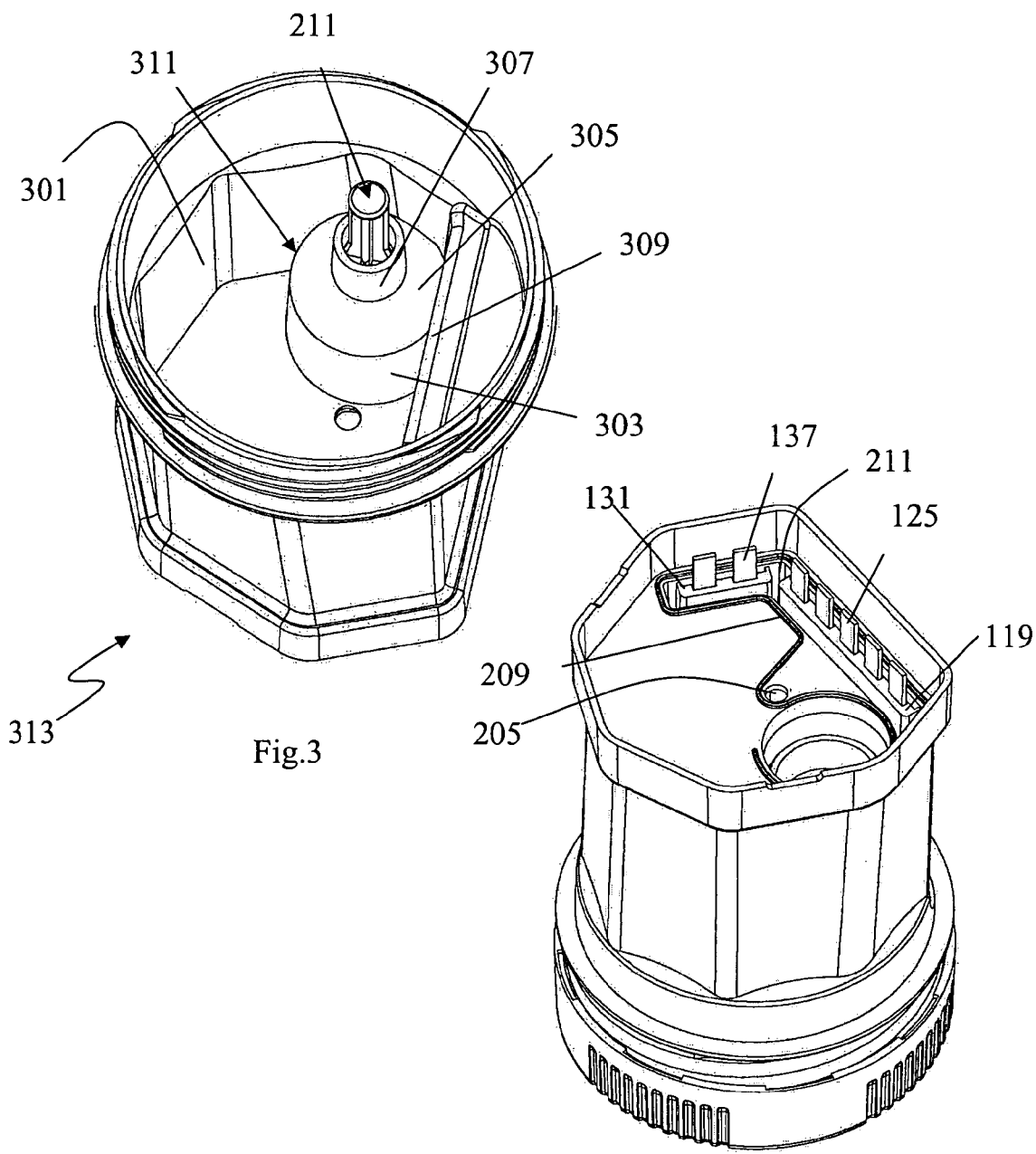
FIG. 3 is a perspective view of the device in accordance with the present invention with a lid removed.
FIG. 4 is a perspective view of the device in accordance with the present invention with a base removed.

Referring to FIGS. 1 and 2, the device of the invention can be used to collect a body fluid, such as urine, and to detect the presence or amount of an analyte contained therein (e.g. a drug of abuse and/or metabolite thereof). The device generally includes a container 111 having an opening 115 for collecting the liquid sample, a lid 101 for closing the opening, and at least one test element 137 for conducting a test. In one embodiment the lid 101 can be a lid that is screwed onto the device to be secured in place, but in other embodiments the lid can be snapped on or otherwise secured in place by any convenient means. The device can also contain a seal 109 for sealing the container shut when the lid 101 is applied. Inside of the first container 111 is provided a movable member, such as a plunger 149 that is movably received in the container 111.

The parts of the device can be formed or molded from any suitable material. For example, a variety of plastics can be used. Referring to the embodiment illustrated in the Figures, the device includes a cup-like main body 111 and a base 151 that can be hermetically attached to a bottom of the main body 111. With reference to FIGS. 3, 5, 7, and 9, the main body 111 has a number of vertical sidewalls 117 connected to each other, a round upper rim 113 connecting top ends of the sidewalls, and a generally flat bottom wall 207 connecting lower ends of the sidewalls. In this embodiment two inner walls 309 extend generally parallel to two adjacent sidewalls 117 and connect with them at top ends thereof, so as to define a second chamber 601, which contains the test element. The upper rim 113 defines an opening 115 for introducing the liquid sample and can have threads that can mate with corresponding threads on the lid 101 during coupling of the lid to the container 313.

Figure 7:
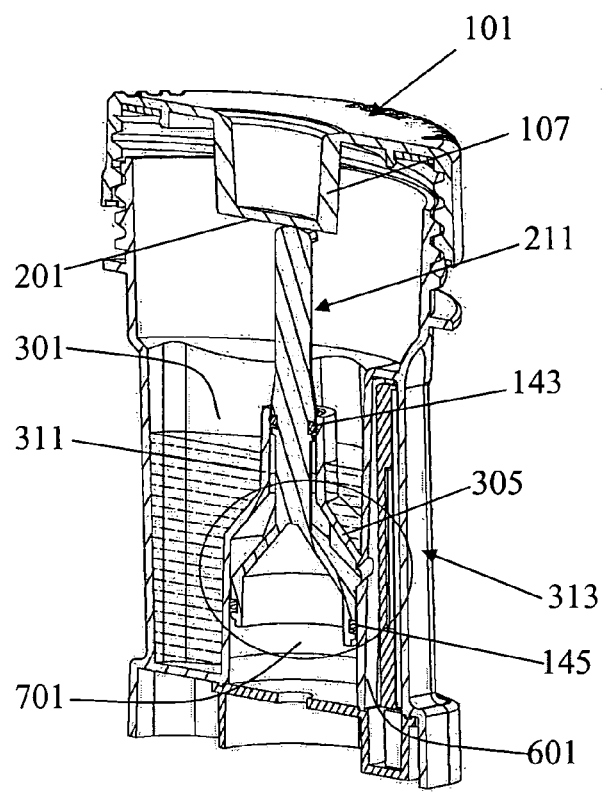
FIG. 7 is a cross-sectional view of the device in accordance with the present invention, showing a plunger is positioned at a first position and the liquid sample is received in only the first chamber.
Figure 8:
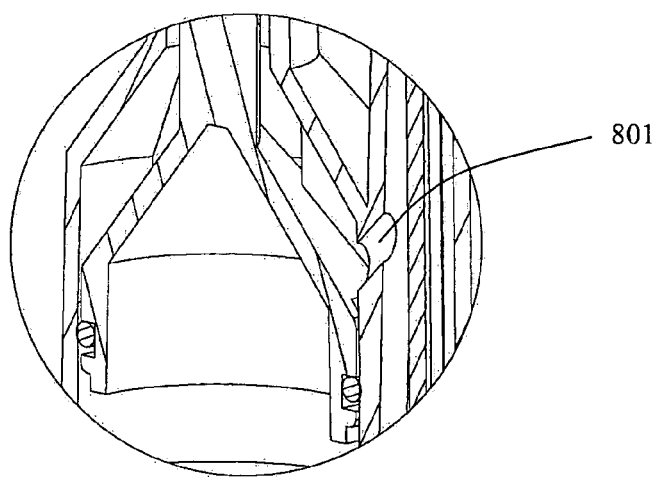
FIG. 8 is an enlarged partial view of FIG. 7, wherein the liquid sample is not shown in order to clearly illustrate the structure of a channel.

The device has a movable member, which can create an air pressure vacuum in certain chambers of the device when it is moved from a first to a second position. In the embodiment illustrated in the Figures, the movable member is a plunger 149. A plunger housing 311 is formed in the interior of the main body 111 and in air communication with the second chamber 211, which contains the test element. The plunger housing 311 forms the third chamber. In this embodiment the plunger housing 311 is shaped like an inverted funnel and includes a cylindrical lower section 303 opening at the bottom wall 207 of the main body 111 through a vent hole. The plunger housing also has a cylindrical upper section 307 which has a diameter smaller than that of the lower section 303, and a tapered intermediate section 305 connecting the upper and lower sections. As shown in FIG. 7 and detailed in FIG. 8, in this embodiment the lower section 303 of the plunger housing is partially connected to one of the inner walls 309, and a channel 801 is defined in the connection area to allow air exchange between the third chamber 701 and the second chamber 601. By two chambers being in "air communication" or "gas communication" is meant that a change in the air pressure in one chamber will cause an air pressure change in the other chamber, or that it will cause fluid to be drawn into or expelled from one chamber to another, or that air is able to move between two (or more) chambers.

Chambers

The chambers of the device can be of any shape or form suitable to fulfill their function in the device. In one embodiment the third chamber can take a generally cylindrical, syringe-like, or funnel shape, but other shapes can also be used that can support the movable member and the first and second zones of the third chamber. Also, the different zones of the third chamber can also take different forms. Similarly, the second chamber can also take any shape that supports the test elements, and the first chamber can be of any shape that supports the introduction of liquid into the device.

The bottom wall 207 of the main body (which forms the bottom of the first chamber) contains a passageway 205 therein connecting the first chamber to the second chamber 601. The passageway 205 has a diameter that is too small to allow the fluid in the main body 111 to flow therethrough under air pressure that is substantially equal to atmospheric pressure. Fluid will flow from the first chamber into the second chamber under a vacuum of air pressure induced by movement of the movable member. In various embodiments the diameter of the passageway is less than 10 mm, or less than 9 mm, or less than 8 mm, or less than 7 mm, or less than 6 mm, or less than 5 mm, or less than 4 mm, or less than 3 mm, or even smaller. In one embodiment, the diameter of the passageway 205 is about 4 mm, or about 5 mm, or about 3 mm, or 3-5 mm. While in the embodiment depicted the passageway is an opening between the first and second chamber, the passageway can also have other configurations. For example, in various embodiments the passageway can be a sinuous groove defined in the bottom wall of the main body with a small sectional diameter, or any opening or passageway connecting the two chambers. The bottom wall 207 further includes an embossment 209 at a bottom surface thereof around the opened area.

The base 151 can be permanently affixed to the main body 111. The base 151 includes an upper wall 153, a bottom wall 213, and a fencing wall 155 connecting the upper wall 153 and bottom wall 213. The fencing wall 155 and bottom wall 213 together define a cavity 157 which is a part of the second chamber 601 and receives a portion of the liquid sample. In this embodiment a groove 159 is defined in a top of the fencing wall 155 to engage with the embossment 209 on the bottom wall 207 of the main body 111. In assembling the main body 111 and the base 151, the embossment 209 can be embedded in the groove 159, and then an ultrasonic welding can be used to hermetically seal these two components. Various other methods can also be used to affix the base and the main body while ensuring a good seal therebetween. In various embodiments, thermal welding, gluing, or compressive ring gaskets all can be used. The base 151 further includes spaced retaining walls 161 for retaining the test element, a block wall 163 to block rapid rate fluid, and a vent hole 165 defined in the upper wall 153. The performance and the function of the retaining walls, block wall, and vent hole will be described in detail below.

The lid 101 can be coupled to the container 313 to seal the sample in the container. Additionally, in the present invention, the coupling of the lid 101 to the container can also can be used to initiate an assay, which will be described in further detail below. In this embodiment the lid 101 includes a top 103 and a downwardly-extending flange 105 which has a shape that corresponding to the shape of the rim 113 of the container 313 so that the flange can couple to the rim. In the embodiment depicted, the top 103 is formed with a circular depression 107 having a bottom surface 201 that can depress the movable member 215 while the lid 101 is being coupled to the container 313. A sealing member 109, such as an O-ring can be positioned between the lid 101 and the container 313 to provide a seal therebetween.

The test element can be in the form of a test card, which can be any type of device that is configured to assay a sample. In this embodiment, the test element includes an assay card 119 for detecting the presence or amount of an analyte in the sample and the device further includes an adulteration test card 131 for detecting the contamination of the sample. Each card 119 (131) has a size and shape that is configured to be inserted into an upper portion 211 of the second chamber 601 of the device, and retained by the retaining walls 161 of the base 151. In other embodiments the card can be retained by any suitable means within the second compartment 601. In various embodiments each card 119 (131) can have a panel 121 (133) with a group of slots 123 (135) defined therein, a number of assay strips 125 or adulteration strips 137 retained in the slots, and a cover 127 (139) adhered to one surface of the panel having windows 129 (141) for observing the test result.

The movable member 215 is movably present in a plunger housing 311. In this embodiment, the movable member is a plunger 215. The plunger 215 includes an elongated push bar 147 extending through the upper portion 307 of the plunger housing 311 toward the opening 115 of the container 313, a plunger body 149 connecting one end of the push bar 147 and having a size and shape that is configured to be movable in the lower portion 303 of the plunger housing 311, and a first sealing ring 143 retained around the push bar 147 and a second sealing ring 145 retained around the plunger body 149. In the embodiment depicted in the Figures the sealing rings 143 and 145 have the form of circular rubber or plastic rings. But the sealing rings can be made of any suitable material and can take any shape that functions within the device.

With reference to FIGS. 5-9, in this embodiment the base 151 is permanently fixed to the main body 111 to form an integral container 313. In this assembled state, a first chamber 301 is defined in the interior of the main body 111 for storing the liquid sample introduced through the opening 115. A second chamber 601 of the main body 111 can also include a cavity portion 157 defined in part by the base 151, and an upper portion 211 for receiving the test element. A passageway 205 is provided to permit the liquid sample to flow from the first chamber 115 to the second chamber 601. The passageway is sized so that the surface tension of the liquid sample will prevent the sample from flowing from the first to the second chamber until it is "pulled" or sucked into the second chamber by the vacuum created by depressing the plunger in the third chamber. In the present embodiment, the passageway 205 is a small size bore as hereinbefore mentioned.

Figure 9:
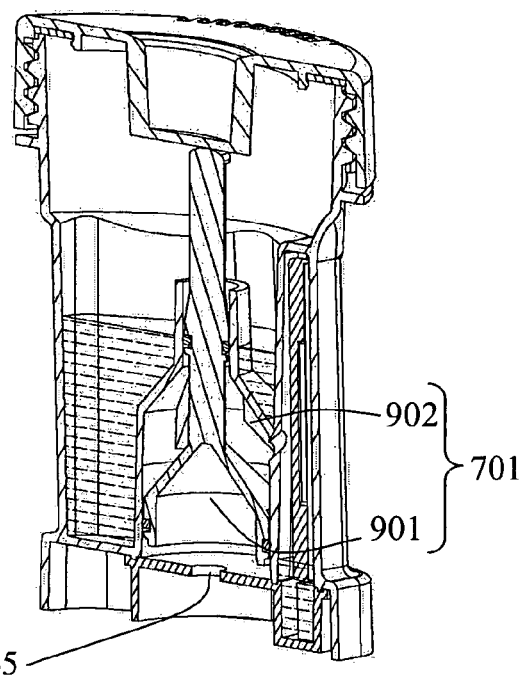
FIG. 9 is a cross-sectional view similar to FIG. 7, wherein the plunger is positioned at a second position, and a portion of liquid sample has flown into the second chamber.

A third chamber 701 is defined in an interior of the plunger housing 311, as shown in FIGS. 7 and 9, when the plunger 311 is received in the plunger housing 311, the first and second sealing rings, 143 and 145 respectively, serve to provide a seal within the third chamber 701. The third chamber 701 contains a first zone 901 and a second zone 902, where the first zone is the area below the movable member and the second zone is the area above the movable member. Therefore, the first and second zones change in volume as the movable member is moved from one position to a second position. When present, the sealing rings can divide the first zone from the second zone of the third chamber. In the embodiment depicted, the first zone 901 is the space in the third chamber below the second sealing ring 145, and the second zone 902 is the space defined above the first sealing ring 145 and below the second sealing ring 143. As the plunger 215 moves in the third chamber 701, the first and second sealing rings, 143, 145 respectively, remain in contact with the inner surface of the upper and lower portions 303, 307, respectively, of the plunger housing 311 to prevent air communication between the first and second zones 901, 902. The channel 801 allows the passage of air from the second chamber to the third chamber as the movable member is lowered in the third chamber. The channel 801 can take any suitable configuration, but is conveniently present as an opening allowing air communication between the second chamber and third chamber.

Method of Use

In use, a liquid sample, such as urine, is first introduced into the first chamber of the container. Liquid sample placed into the first chamber 115 will remain in the first chamber and will not flow through the passageway 205 since the surface tension of the liquid sample is sufficient to prevent it from flowing through the passageway, until drawn through by a vacuum force created in the second chamber 601.

The lid 101 is then coupled to the container 313, such as by screwing the lid onto the container. With reference to FIG. 7, the plunger 215 is located at a first, raised position at the beginning of the assay. In the first position, the top of the push bar 147 extends upward a sufficient distance in the first chamber so that when the lid is applied, the depression 107 in the lid will contact the top of the push bar. The plunger body 149 is located in the lower section 303 of the plunger housing 311. In one embodiment the plunger body 149 abuts against a number of ribs projecting from an inner surface of the intermediate section 305. When the plunger is in the first, raised position, the volume of air in the second zone 902 of the third chamber 701 is relatively small relative to the volume of air in the second zone 902 when the plunger body 149 is in the second, lowered position.

When the lid 101 is screwed onto the container, the bottom surface 201 of the circular depression 107 comes into contact with the top of the push bar 147, and exerts a downward force on the push bar to actuate movement of the plunger along its axial direction from the first, raised position to the second, lowered position. With the movement of the plunger from the first position to the second position, air is forced from the first zone out of the vent hole. At the same time, a vacuum is created in the second zone, which causes air to be "pulled" in from the second chamber 601 into the second zone of the third chamber to fill the vacuum. This action thereby also creates a corresponding vacuum in the second chamber 601, which "pulls" fluid sample in the first chamber 115 through the passageway 205 and into the second chamber 601 to neutralize the vacuum, since the force of the vacuum is sufficient to overcome the surface tension of the liquid sample over the passageway. This therefore causes the fluid sample to contact the test elements in the upper portion 211 of the second chamber. The vent hole can be conveniently configured as an opening that allows the passage of air, but can also take any other suitable configuration consistent with its function.

Figure 5:
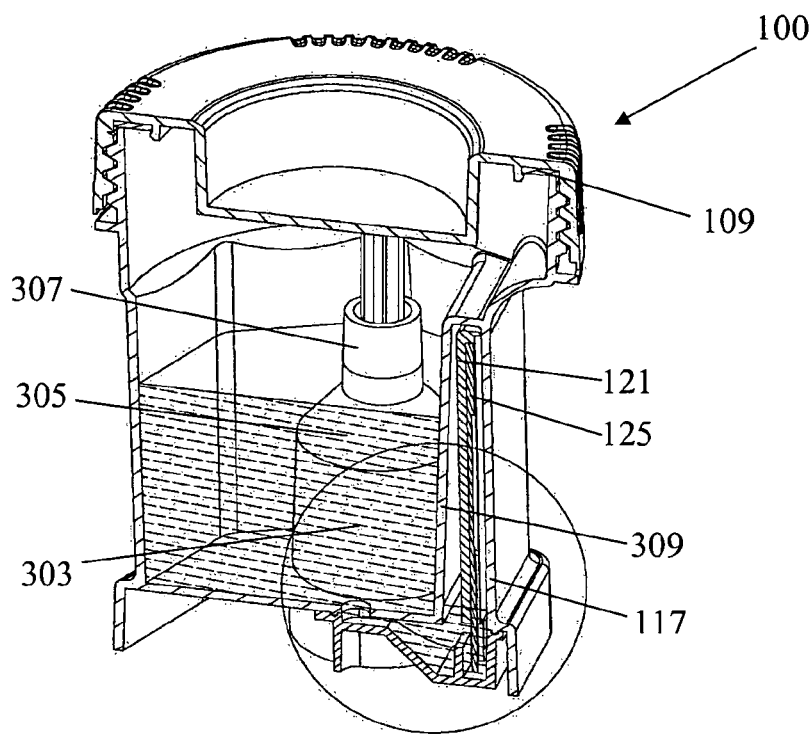
FIG. 5 is a cross-sectional view of the device in accordance with the present invention, wherein a liquid sample is received in both first and second chambers.
Figure 6:
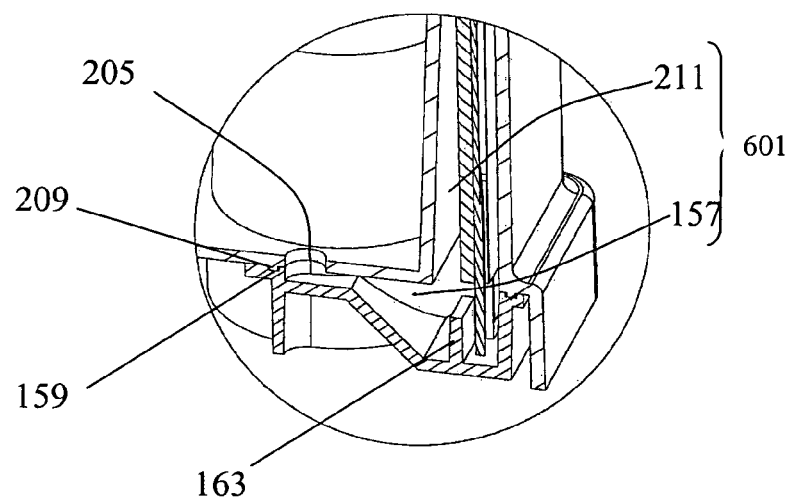
FIG. 6 is an enlarged partial view of FIG. 5, wherein the liquid sample is not shown in order to clearly illustrate the structure of a passageway.

Referring to FIGS. 5 and 6, in one embodiment a barrier wall 163 is located directly in the flow path of fluid coming into the second chamber from the first chamber. This barrier wall 163 serves to block a portion of the liquid sample that enters the second chamber 601 and prevents the liquid sample from achieving a flow rate high enough to cause damage to the strips 125, 137 or flooding thereof. The barrier wall 163 requires the fluid to turn at a right angle before contacting the test strips, therefore causing the liquid sample to slow down and contact one end of each strip 125, 137 in a more orderly fashion. This facilitates the liquid sample advancing through the test strip by capillary action to the test line, and a visible result is shown in the result window 129, 141. The sidewalls 117 of the container 313 can be transparent or semi-transparent to enable visual observation of the strips therethrough.

As shown in FIG. 9, when the plunger 211 is moved from the first position to the second position, the liquid sample drawn into the second chamber 601 is of a volume that adequately submerges the test strips but does not cause flooding. The plunger 211 can be set during manufacture so that movement from the first position to the second position draws in an appropriate amount of liquid sample. Additionally, the first position can also be preset in manufacture, but the second position can be controlled by the user. For example, a mark can be provided as an indicator on the rim 113 to indicate that when the lid 101 screws to this line the plunger has reached the second position. In this embodiment, the second position can be reached when the lid 101 is completely coupled to the container 313. Thus, the user can begin the assay in a single step of securing the lid to the container, and the test can be performed.

Example 1

This example illustrates the general use of a device of the invention. Water was poured into five devices of the invention configured as urine cups. After one hour the water sample remained in the first chamber of the cup and had not entered the second chamber by passing through the passageway. The lids were then applied to the cups, thereby pressing down the push bar and moving the plunger from the first position to the second position as the lid was applied.

After 5 minutes, it was observed that water had entered the second chamber through the passageway. The water sample wetted the test strips without flooding them. The cup was then placed into a barometric container and subjected to a barometric pressure of 0.7 for 3 minutes. No leaking was observed to occur.

Example 2

This example illustrates the use of a device of the invention to detect drugs of abuse in human urine using a competitive assay. Thus, a line would appear at the test line when no analyte was present in the sample. A test strip was included to test for the following analytes: THC, opiates (OPI), PCP, and methamphetamine (MET).

Samples of drug-free urine, urine at −50% cutoff, urine at +50% cutoff, and 3× cutoff were arranged. Each sample was analyzed in triplicate using a device of the invention by placing the urine sample in the cup and fastening the lid, thus beginning the assay.

At 5 minutes of time, the results were observed. In the drug-free urine sample, a bright line was observed on the test line of all analytes for all three replicates, indicating a negative result for all analytes. In the −50% cutoff, a sample a line was observed for all analytes in all three replicates, indicating a negative result for all analytes. In the +50% cutoff samples, either no line or a very faint line appeared in each of the three replicates, indicating a positive result for all samples. In the 3× cutoff samples, no line was visible indicating a positive result.

The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The invention claimed is:

1. A device for detecting the presence of an analyte in a liquid sample, comprising:
    an opening for introducing the liquid sample into a first chamber for collecting the liquid sample;
    a second chamber connected to the first chamber by a first passageway and containing a test element;
    a third chamber connected to the second chamber by a second passageway and containing a plunger, the plunger comprising a push bar and having first and second positions, the third chamber being divided by the plunger into first and second zones; the plunger in contact with at least one wall of the third chamber to prevent gas communication between the first and second zones; and
    a lid for closing the opening, wherein the lid contacts the push bar and moves the plunger from the first position to the second position when the opening is sealed with the lid, wherein movement of the plunger from the first position to the second position causes a volume of air to be drawn from the second chamber into the second zone of the third chamber via the second passageway, thereby causing a volume of the liquid sample to be drawn from the first chamber through the first passageway into the second chamber to contact the test element, wherein the first zone of the third chamber is fluidly sealed from the second chamber in the second position of the plunger, and wherein the device is fluidly sealed when the opening is sealed with the lid.

2. The device of claim 1 wherein the test element is an assay card containing one or more test strips.

3. The device of claim 1 wherein the plunger contains a seal in contact with at least one wall of the third chamber to prevent gas communication between the first and second zones.

4. The device of claim 1 wherein the third chamber comprises a bottom and a vent hole is situated on the bottom of the third chamber.

5. The device of claim 1 wherein the passageway has a diameter of less than 8 mm.

6. The device of claim 5 wherein the passageway has a diameter of less than about 4 mm.

7. The device of claim 1 wherein the test element comprises at least one test strip.

8. A method for detecting the presence of an analyte in a liquid sample, comprising:
   a) introducing a liquid sample into a test device comprising:
      an opening for introducing the liquid sample into a first chamber for collecting the liquid sample;
      a second chamber connected to the first chamber by a first passageway and containing a test element;
      a third chamber connected to the second chamber by a second passageway and containing a plunger, the plunger comprising a push bar and having first and second positions, the third chamber being divided by the plunger into first and second zones; the plunger in contact with at least one wall of the third chamber to prevent gas communication between the first and second zones; and
      a lid for closing the opening, wherein the lid contacts the push bar and moves the plunger from the first position to the second position when the opening is sealed with the lid, and wherein the device is fluidly sealed when the opening is sealed with the lid;
   b) causing the movable member to move from the first position to the second position and thereby causing a volume of air to be drawn from the second chamber into the second zone of the third chamber via the second passageway, and thereby causing a volume of the liquid sample to be drawn from the first chamber through the first passageway and into the second chamber to contact the test element, wherein the first zone of the third chamber is fluidly sealed from the second chamber in the second position of the plunger; and
   c) detecting the presence of the analyte in the sample.

9. The method of claim 8 wherein the test element comprises at least one test strip.

10. The method of claim 8 wherein depressing the push bar and moving the plunger from the first position to the second position causes a negative air pressure gradient to form in the third chamber and the volume of air to be drawn from the second chamber into the third chamber.

11. The method of claim 10 wherein the movement of the volume of air from the second chamber to the third chamber causes a negative air pressure gradient to form in the second chamber.

12. The method of claim 11 wherein the negative air pressure gradient in the second chamber causes the fluid sample to flow from the first chamber through the passageway to the second chamber, and thereby to contact the test element.

13. The method of claim 8 wherein depressing the push bar and moving the plunger from the first position to the second position causes a volume of air to escape from the first zone through a vent hole.

\* \* \* \* \*